United States Patent [19]

Miller et al.

[11] Patent Number: 5,091,410
[45] Date of Patent: Feb. 25, 1992

[54] THIOXANTHENONE ANTITUMOR AGENTS

[75] Inventors: Theodore C. Miller, East Greenbush, N.Y.; Michael E. Ross, Haverford Township, Delaware County, Pa.

[73] Assignee: Sterling Winthrop Inc., New York, N.Y.

[21] Appl. No.: 713,172

[22] Filed: Jun. 10, 1991

[51] Int. Cl.$^5$ ..................... A61K 31/38; C07D 335/16
[52] U.S. Cl. ....................... 514/437; 549/27; 514/908
[58] Field of Search .................. 549/27, 392; 514/437, 514/454, 908

[56] References Cited

U.S. PATENT DOCUMENTS 3,577,441  5/1971  Kaminsky et al. ..................... 549/27
3,577,558  5/1971  Rosi ....................... 549/27
4,582,851  4/1986  Worth ................. 514/437

OTHER PUBLICATIONS

Blanz & French, "A Systematic Investigation of Thioxanthen-9-ones and Analogs as Potential Antitumor Agents", *J. Med. Chem.*, 6, 185-191 (1963).

*Primary Examiner*—Glennon H. Hollrah
*Assistant Examiner*—Mark W. Russell
*Attorney, Agent, or Firm*—Philip E. Hansen; Paul E. Dupont

[57] ABSTRACT

1-[[(Dialkylamino)alkyl]amino]-4-substituted-thioxanthen-9-ones are disclosed as antitumor agents. Compositions containing the thioxanthenones and methods of treating tumors and cancer in mammals with the thioxanthenones are also disclosed.

9 Claims, No Drawings

THIOXANTHENONE ANTITUMOR AGENTS

FIELD OF THE INVENTION

The present invention relates to novel 1-[[(dialkylamino)-alkyl]amino]-4-substituted-thioxanthen-9-ones, to pharmaceutical compositions containing the thioxanthenones, to methods of treating tumors with the thioxanthenones and to methods of treating cancer in mammals with the compositions containing the thioxanthenones.

INFORMATION DISCLOSURE STATEMENT

Rosi U.S. Pat. No. 3,577,558 (1971) discloses 1-[[2-(diethylamino)ethyl]amino]-4-(alkoxymethyl)-thioxanthen-9-one ethers.

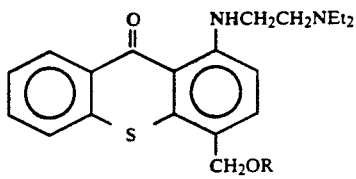

The compounds are stated to be schistosomacidal agents.

Blanz and French [*J. Med. Chem.* 6, 185–191 (1963)] disclose the synthesis of a series of thioxanthenones related to lucanthone and the results of the testing of the compounds against a leukemia and two solid tumors. Among the compounds disclosed are

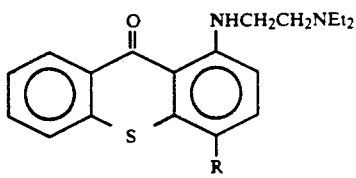

wherein R is methyl, methoxyl, and ethoxyl.

SUMMARY OF THE INVENTION

In a product aspect the invention relates to compounds of the formula I

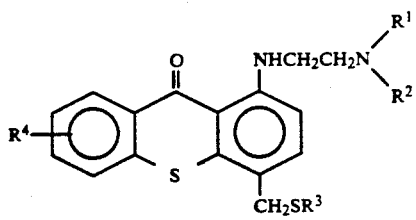

or acid addition salt or solvate thereof wherein n is two or three, preferably two; $R^1$ and $R^2$ are independently lower-alkyl, preferably both are ethyl; $R^3$ is lower-alkyl and $R^4$ is hydrogen, lower-alkyl, lower-alkoxy or halogen. The compounds are useful for the treatment of tumors in mammals.

Lower-alkyl as used herein describes linear, branched or cyclic hydrocarbons containing four or fewer carbon atoms. Halogen describes bromine, chlorine or fluorine.

In a further product aspect the invention relates to compositions for treating tumors and cancer in mammals which comprise compounds of formula I together with pharmaceutically acceptable excipients or diluents.

In a process aspect the invention relates to a method for treating tumors in mammals which comprises administering to the mammal a compound of formula I.

In a further process aspect the invention relates to a method for treating cancer in a mammal which comprises administering to the mammal a composition of a compound of formula I together with pharmaceutically acceptable excipients or diluents.

DETAILED DESCRIPTION INCLUSIVE OF PREFERRED EMBODIMENTS

The synthesis of compounds of the invention may be outlines as shown in Scheme A:

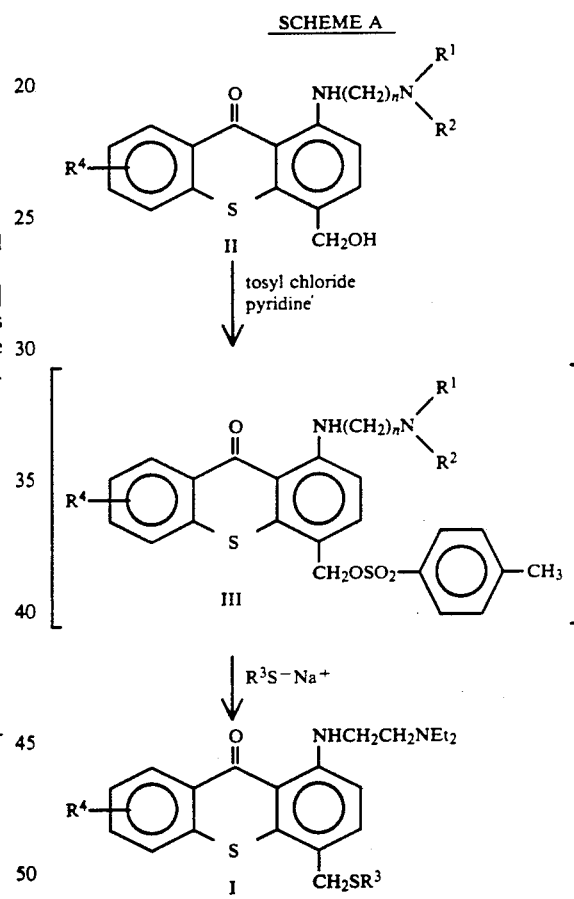

The compounds of formula I may be synthesized by reacting the appropriate alcohol (II) with about one equivalent of p-toluenesulfonyl chloride in pyridine at 0° to 80°, preferably about 25°, to produce the sulfonate ester III, which is not isolated but, rather, is reacted immediately with an excess, preferably about 5–7 fold excess, of a salt of the appropriate thiol. The preferred salt is the sodium salt and the reaction is carried out in a suitable solvent, preferably DMSO.

The appropriate alcohols may be obtained by procedures well known in the art, particularly as described in U.S. Pat. Nos. 3,711,512 and 3,294,803 which are incorporated herein by reference.

The compounds of formula I are useful both in the free base form and in the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet and nuclear magnetic resonance spectroscopy. The course of the reactions and the identity and homogeneity of the products were assessed by thin layer chromatography (TLC) or gas-liquid chromatography (GLC). The melting points are given in degrees C and are uncorrected. The starting materials are either commercially available or may be prepared by procedures well known in the art.

EXAMPLE 1

1-[[2-(Diethylamino)ethyl]amino]-4-(methylthiomethyl) thioxanthen-9-one (I: $R^1 = R^2 = Et$; $R^3 = $ methyl; $R^4 = H$; $n=2$)

A mixture of 17.9 g (50 mmol) of 1-[[2-(diethylamino)-ethyl]amino]thioxanthen-4-methanol and 9.6 g (50 mmol) of p-toluenesulfonyl chloride in 125 mL of pyridine was stirred for 2 hours at room temperature. The reaction was diluted with 100 mL of DMSO and the pyridine was removed on a rotary evaporator. A slurry of 300 mmols of the sodium salt of methanethiol in 100 mL of DMSO, preformed from 16.8 g of methanethiol and 12.0 g of 60% NaH in mineral oil, was added. The reaction was stirred for 2 hours and poured into 1.5 L of water. The resulting gum was removed, dissolved in chloroform, washed with 5% aqueous NaOH, dried over $Na_2SO_4$, filtered and stripped. The residue was digested with ethyl acetate and filtered to remove unreacted starting material. The solution was chromatographed on alumina eluting with a gradient from 0 to 1% isopropylamine in 95:5 pentane/methylene chloride then isopropylamine in 90:10 pentane/methylene chloride to obtain 7 g of product which was recrystallized from ethyl acetate to yield 6.6 g of product, mp 125°–127°.

It is contemplated that other members of the genus I may be made in a fashion analogous to that of Example 1, substituting the appropriate 1-[[2-(dialkylamino)ethyl]amino]- or 1-[[3(dialkylamino)propyl]amino]thioxanthen-4-methanol for 1-[[2(diethylamino)ethyl]amino]thiioxanthen-4-methanol and the appropriate alkylthiol for methanethiol.

A representative example of the invention was tested for antitumor activity in mice according to the following procedure:

The animals were pooled, implanted subcutaneously with 30 to 60 mg tumor fragments by 12-gauge trocar, and again pooled before unselective distribution to the various treatment and control groups. For early-stage treatment, chemotherapy was started within 1 to 5 days after tumor implantation while the number of cells was relatively small ($10^7$ to $10^8$ cells). For advanced-stage treatment, chemotherapy was delayed until the tumor become relatively large (200 to 300 mg in size). A 300-mg tumor contains approximately $3 \times 10^8$ total cells. Tumors within a given advanced-stage trial were within a 2.5-fold size range for 90% of the animals. Tumors were measured with a caliper weekly (or twice weekly for the more rapidly growing tumors). Mice were sacrificed when their tumors reached 1500 mg (i.e., before they can cause the animal discomfort). Tumor weights were estimated from two-dimensional, measurements.

The treatment and control groups were measured when the control group tumors reached approximately 700 to 1200 mg in size (Median of Group). The median tumor weight of each group was determined (including zeros). The T/C value in percent is an indication of antitumor effectiveness: A T/C equal to or less than 42% is considered significant antitumor activity by the Drug Evaluation Branch of the Division of Cancer Treatment (NCI). A T/C value < 10% is considered to indicate highly significant antitumor activity. A body weight loss nadir (mean of group) of greater than 20% or greater than 20% drug-deaths is considered to indicate an excessively toxic dosage.

The results are shown in Table I for pancreatic ductal adenocarcinoma #03.

TABLE 1

| Example # | T/C (%) | Weight Loss (g)* | Drug Deaths | Total Dose (mg/kg) i.v. |
|---|---|---|---|---|
| 1 | 0 | 2.0 | 0 | 1830 |

*average body weight was 25 g

The pharmaceutical compositions of the present invention include one or more of the compounds of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

The percentage of active component in the composition and method for treating tumors or cancer can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus be determined by the clinician considering all criteria and utilizing his best judgement on the patient's behalf.

We claim:

1. A compound of formula

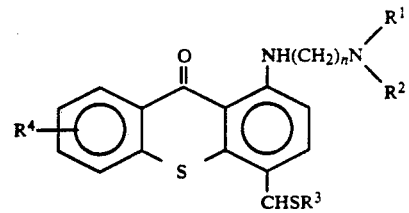

wherein
n is 2 or 3;
$R^1$ and $R^2$ are independently lower-alkyl;
$R^3$ is lower-alkyl; and
$R^4$ is hydrogen, lower-alkyl, lower-alkoxy or halogen.

2. A compound according to claim 1 wherein n is 2 and both of $R^1$ and $R^2$ are ethyl, and $R^4$ is hydrogen.

3. 1-[[2-(Diethylamino)ethyl]amino]-4-[(methylthio)-methyl]-thioxanthen-9-one according to claim 2.

4. A pharmaceutical composition which comprises a compound of claim 1 and a pharmaceutically acceptable carrier or diluent.

5. A pharmaceutical composition which comprises the compound of claim 3 and a pharmaceutically acceptable carrier or diluent.

6. A method for treating a tumor in a mammal which comprises administering to said mammal an amount of a compound of claim 1 effective to reduce the size of said tumor.

7. A method for treating a tumor in a mammal which comprises administering to said mammal an amount of the compound of claim 3 effective to reduce the size of said tumor.

8. A method for treating cancer in a mammal which comprises administering to a mammal suffering from said cancer a tumor-size-reducing amount of a composition according to claim 4.

9. A method for treating cancer in a mammal which comprises administering to a mammal suffering from said cancer a tumor-size-reducing amount of a composition according to claim 5.

* * * * *

UNITED STATES PATENT AND TRADEMARK OFFICE
CERTIFICATE OF CORRECTION

PATENT NO. : 5,091,410
DATED : February 25, 1992
INVENTOR(S) : Theodore C. Miller et al.

It is certified that error appears in the above-identified patent and that said Letters Patent is hereby corrected as shown below:

Column 1, line 20, the information to the right of the formula was omitted and should read as follows: -- R=methyl, ethyl, N-propyl, isopropyl and n-hexyl --.

Column 1, line 50, formula I, the portion of the formula reading

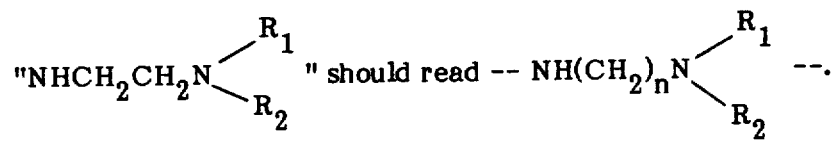

Column 2, line 15, the word "outlines" should read as -- outlined --.

Column 2, line 16, Scheme A, formula I, the portion of the formula

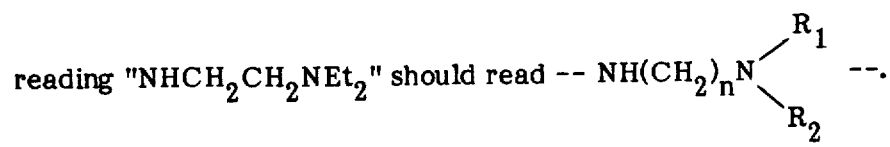

UNITED STATES PATENT AND TRADEMARK OFFICE
CERTIFICATE OF CORRECTION

PATENT NO. : 5,091,410

DATED : February 25, 1992

INVENTOR(S) : Theodore C. Miller et al.

It is certified that error appears in the above-identified patent and that said Letters Patent is hereby corrected as shown below:

Column 6, line 15, Claim 1, the portion of the formula reading "$CHSR^3$" should read -- $CH_2SR^3$ --.

Signed and Sealed this

Seventh Day of September, 1993

Attest:

BRUCE LEHMAN

Attesting Officer

Commissioner of Patents and Trademarks